(12) United States Patent
Takebe et al.

(10) Patent No.: US 6,517,831 B2
(45) Date of Patent: Feb. 11, 2003

(54) PRODUCT CONTAINING HEALTHFUL COMPONENT AND PROCESS FOR PREPARING THE SAME

(75) Inventors: Minoru Takebe, Tokyo (JP); Jitsuo Shiraishi, Tokyo (JP)

(73) Assignee: Nichimo Co., Ltd., Tokyo (JP)

( * ) Notice: Subject to any disclaimer, the term of this patent is extended or adjusted under 35 U.S.C. 154(b) by 0 days.

(21) Appl. No.: 09/902,040

(22) Filed: Jul. 10, 2001

(65) Prior Publication Data

US 2002/0012659 A1 Jan. 31, 2002

Related U.S. Application Data

(62) Division of application No. 09/194,657, filed as application No. PCT/JP98/01507 on Apr. 1, 1998, now Pat. No. 6,303,161.

(30) Foreign Application Priority Data

Apr. 1, 1997 (JP) .............................................. 9-83036

(51) Int. Cl.$^7$ .............................................. A61K 35/84
(52) U.S. Cl. .............................. 424/93.45; 424/195.15; 424/195.16; 424/780; 424/400; 424/93.1; 435/254.3; 435/252.9
(58) Field of Search .............................. 435/171, 252.9, 435/254.3; 424/780, 725, 195.15, 195.16, 400, 93.1, 93.45

(56) References Cited

U.S. PATENT DOCUMENTS 4,308,284 A * 12/1981 Noda et al.
5,965,178 A * 10/1999 Baensch et al.
6,045,819 A * 4/2000 Takebe

* cited by examiner

Primary Examiner—Leon B. Lankford, Jr.
Assistant Examiner—Ruth A. Davis
(74) Attorney, Agent, or Firm—Koda & Androlia (57) ABSTRACT

A product which contains a health-promoting component and a process for preparing such a product, in the present invention, using a pulse crop as a raw material. The product accomplishes health promotion very effectively by means of at least one member of the group consisting of liver function improving constituents, cardiac function improving constituents, anti-inflammatory constituents, antifat constituents, antioxidation consititents, antimutagen constituents, and components which have an intestine-regulating effect in single-stomached animals; and the method produces such a product with good efficiency. The product of the present invention can be used directly "as is"; and alternatively, specified components may be concentrated or may be usefully utilized in applied products which use the product of the present invention as a raw material, e.g., food products, livestock feeds, pet foods or drug raw materials, etc. In miso and soy sauce, since salt is added following the koji preparation step, they are high in salt content and lack all-purpose utility; and in addition, since the aging period following the koji preparation step is extremely long, there are problems in productivity. However, the product of the present invention is easy to manufacture and is also a low-cost product.

9 Claims, 4 Drawing Sheets

PRODUCT CONTAINING HEALTHFUL COMPONENT AND PROCESS FOR PREPARING THE SAME

This is a Divisional Application of application Ser. No. 09/194,657, filed Nov. 30, 1998 now U.S. Pat. No. 6,303,161, which is the National Stage of application No. PCT/JP98/01507, filed Apr. 1, 1998.

TECHNICAL FIELD

The present invention relates to a product containing a healthful or salutary component and a process for preparing the same. In particular, the product of the present invention is prepared from a pulse crop as a starting material. The term "pulse crop" used herein means leguminous crops such as soybeans, defatted products and hycopotyls thereof, soy protein extracts, soy protein isolates and so forth, and the term "product" means products as such (plain products) which are made from a pulse crop as a starting material, applied products containing the plain product as an ingredient, for example, foods, livestock feeds and aquacultural feeds, cosmetics, diets of pets, and precursory products for pharmaceutical preparations.

BACKGROUND ART

In general, soybean, which is one of the pulse crops, contains isoflavone compounds including daidzin, daidzein, genistin and genistein.

The isoflavone compounds are represented by the following formula and Denotative Table.

Denotative Table

|  | R1 | R2 |
|---|---|---|
| daidzin | H | glucose |
| daidzein | H | H |
| genistin | OH | glucose |
| genistein | OH | H |

Of these isoflavone compounds, daidzein is an aglycone of daidzin having its glucose as a glycosidic saccharide hydrolytically separated therefrom, and genistein is an aglycone of genistin having its glucose as a glycosidic saccharide hydrolytically separated therefrom. With respect to the isoflavone compounds, contents thereof and percentages between daidzin and daidzein and between genistin and genistein in a defatted soybean are shown in the following Table 1.

TABLE 1

|  | daidzin | daidzein | genistin | genistein |
|---|---|---|---|---|
| defatted soybean | 100 (96.9%) | 3.2 (3.1%) | 180 (97.7%) | 4.2 (2.3 &) |

(unit: mg/100 g)

It is understood from Table 1 that, in soybeans, daidzin and genistin are contained in large amounts while daidzein and genistein which are aglycones thereof are contained in smaller amounts.

On the other hand, it has been reported that a glycosidic saccharide is hydrolyzed from an isoflavone compound contained in soybeans to form an aglycone in the course of soy sauce or miso (fermented soybean paste) preparation [see Kihara, K.: Journal of Japan Soy Sauce Research Institute (for SHO-KEN), 16, 5, 190(1990)].

According to this report, although hydrolysis of a glycosidic saccharide proceeds to some extent in cooking of a defatted soybean or in a koji preparation step (seigiku step), most of the saccharide has already hydrolytically been separated in soy sauce cake or a soybean miso. However, since these are highly salinized, ingesting these in large quantities should be avoided. Accordingly, it is difficult to employ any process for preparing these as a process for preparing a food from a pulse crop as a starting material.

Soyasaponins occur in soybeans. For example, in a defatted soybean, soyasaponins occur in an amount of 500 to 700 mg/100 g. It has been reported that soyasaponins consist of 5 varieties of saponins, i.e., soya saponin I, soya saponin II, soya saponin III, soya saponin A1 and soya saponin A2 in the form of a mixture [see Kitagawa et al.: YAKUGAKU ZASSHI, 104, 2, 162–168(1984)]. Each of these has glucuronic acid as a glycosidic saccharide, and the aglycone which is such a compound that the glycosidic saccharide is removed therefrom includes two varieties of soyasapogenol A and soyasapogenol B. In general, however, the aglycone is present as soyasapogenol B. In a commercially available soybean miso, however, neither soyasapogeriol A nor soyasapogenol B was detected.

Further, many reports have been made on pharmacological activities of various constituents contained in pulse crops.

For example, a Pueraria lobata Ohwi (kudzu), which is a type of legume, has been used for a long time as a material for an infusion of Pueraria root (*Puerariae Radix*) as an herb medicine. It has been reported that isoflavone compounds and saponins contained in Pueraria root have liver function improving effects (therapeutic activities against hepatopathy) [see "Nohara et al.: Journal of Medical and Pharmaceutical Society (for WAKAN-YAKU),. 5, 408–409 (1988", "Y. Niiho et al.: YAKUGAKU ZASSHI., 109, 6, 424–431(1989)" and "Y. Niiho et al.: YAKUGAKU ZASSHI., 110, 8, 601–611(1990)"]. More specifically, an alcohol concentration, an acetaldehyde concentration and a concentration of ketones in blood can be lowered to prevent hangovers, nasty aftereffects of drinking or the like, and metabolic dysfunction of the liver can be prevented. Further, it has been reported that soyasaponins contained in soybeans have an anti-inflammatory effect, and can reduce serum cholesterol, neutral fats and phospholipids (cardiac function improving, lipotropic, antidiabetic, antifat, and flesh reducing effects) as well as the above-described effect in common with pueraria root [see Ohminami et al.: EIYO TO SHOKURYO., 34, 2, 105–108(1981)]. It is said that although soyasaponins have the effect of improving functions of a living body as described above, soyasaponins in the form of a glycoside can not be absorbed in a body. Accordingly, saponins in the form of a glycoside are not intestinally absorbable until they are decomposed into an aglycone, i.e., soyasapogenol B by enterobacteria having β-glucuronidase effect. It is said that the decomposition takes a lot of time and thus the aglycone has little chance of being absorbed by a small intestine to lead to an extremely low absorption efficiency. On the other hand, the enterobacteria having β-glucuronidase effect is not regarded as useful enterobacteria. Accordingly, placing no reliance on the decomposition by the enterobacteria, it is desired that soyasaponins be preliminarily decomposed in vitro into soyasapogenol B to ingest the latter. The same desire is true of the soy isoflavone compounds.

Further, soyasapogenol B is a triterpene compound and effective as an endotherine (ET) converter enzyme inhibitor (see Japanese Patent Application Laid-Open (Kokai) No. H7(1995)-188033) and inhibits an endotherine converter enzyme from exhibiting its function, and hence soyasapogenol B is effective as a remedy for endotherine (ET)-related disorders such as hypertension, cerebrovascular contraction after subarachnoid hemorrhage, myocardial infarction, arteriosclerosis, heart failure,renal failure, asthma, and so forth. Further, the triterpene compound has a lipase inhibitory effect and a glycerophosphate dehydrogenase inhibitory effect. Accordingly, the triterpene compound is capable of inhibiting the decomposition of lipids to prevent the lipids from being absorbed in a body, and thus, it is effective for the prevention and treatment of obesity (see Japanese Patent Application Laid-Open (Kokai) Nos. H9(1997)-40689 and H9(1997)-67249) and expected to improve cardial functions and to reduce flesh. Therefore, it is desired that soyasaponins be decomposed to obtain soyasapogenol B as an aglycone of saponins.

Moreover, it has been reported that free myo-inositol and the like, which are formed by the decomposition of phytic acid in soybeans, have a liver function improving effect of facilitating lipometabolism in a liver (therapeutic activities against hepatopathy) (see Kubota, H.: FOOD CHEMICAL, 8, 83–89 (1987).

A further description will be made on promoting liver functions. It has been reported that miso soup has an anti-cancer effect, and this is because the enzyme activity of a liver is enhanced by the ingestion of miso soup [see Kanke, S.: SHOKU NO KAGAKU, 224, 50–54(1996)]. More specifically, it is reported that when iron as a carcinogen and oxidant and miso are fed to a rat or mouse, glutathione-s-transferase (GST) activity is increased. GST has been known to combine a carcinogen with glutathione to form a glutathione conjugate, which is excreted from a body. It is said that phase II xenobiotic-metabolizing enzymes to enhance carcinogen detoxication and elimination such as NAD(P)H: quinone oxidoreductase (DT diaphorase) and aldehyde dehydrogenase, as well as conjugating enzymes such as GST and UDP-glucuronosyl-transferase.

Accordingly, many proposals concerning isoflavone compounds contained in soybeans are disclosed in Japanese Patent Application Laid-Open (Kokai) Nos. S62(1987)-126186, H1(1989)-258669, H5(1993)-170756, and so on.

DISCLOSURE OF THE INVENTION

According to the process described in Japanese Patent Application Laid-Open (Kokai) No. S62(1987)-126186, however, most of the resulting isoflavone compounds are daidzin and genistin which each has a glycosidic saccharide, and aglycones are contained in the resultant in small amounts. Thus, it is impossible to obtain foods and the like which have an excellent pharmacological effect as described above.

The process in Japanese Patent Application Laid-Open (Kokai) No. H1(1989)-258669 comprises hydrolytically separating a glycosidic saccharide from an isoflavone compound by the action of β-glucosidase which is one of the enzymes contained in soybeans. However, aglycones are formed in a small proportion.

The process described in Japanese Patent Application Laid-Open (Kokai) No. H5(1993)-170756 is one which comprises extractively separating isoflavone compounds from aglycones of the isoflavone compounds formed in soy sauce cake or soy sauce. Although the aglycones of the isoflavone compounds are formed in the course of soy sauce preparation in a very high proportion as described above, there is the following disadvantage. That is, the aglycones of the isoflavone compounds are present in soy sauce cake because of their insolubility, and soy sauce cake per se does not serve as a food. Accordingly, the process cannot be employed as a process for preparing a food. Further, aglycones of isoflavone compounds are also formed in a soybean miso at the initial stage of preparation. However, soybean miso has a problem in that it is a highly salinized food and therefore ingesting soybean miso in large quantities should be avoided.

With respect to a soybean miso (mame miso), a rice miso (kome miso), Daitokuji Soy nuggets (Daitokuji-natto: a Japanese fermented soy-food in the form of nuggets), dried-frozen tofu (Kori-tofiu—tofu: a Japanese food made of soy milk curds) and yuba (yuba: a Japanese food made of a film which forms on a surface of thick soy milk when the soy milk is gently heated) as commercially available foods made from a pulse crop as a starting material, contents of daidzin and daidzein and contents of genistin and genistein were comparatively measured. The results are as shown in the following Table 2.

TABLE 2 unit: mg/100 g

|  | daidzin | daidzein | genistin | genistein |
|---|---|---|---|---|
| soybean miso | not detected | 78 | not detected | 57 |
| rice miso | 0.66 | 21 | 2.3 | 20 |
| Daitokuji-natto | not detected | 49 | not detected | 42 |
| dried-frozen tofu | 0.95 | 8.4 | 8.0 | 11 |
| yuba | 110 | 24 | 160 | 17 |

(detection limit: 0.5 mg/100 g)

It is understood from Table 2 that in the soybean miso, the rice miso and the Daitokuji-natto each of which has been subjected to fermentation treatment, daidzin and genistin have substantially been hydrolyzed, and in particular, the soybean miso and the Daitokuji-natto contain daidzein and genistein which are aglycones of daidzin and genistin in large amounts. However, soybean miso and Daitokuji-natto should not be ingested in large amounts because of their high salt contents. It is also understood that in the dried-frozen tofu, each of daidzin, daidzein, genistin and genistein is contained in a small amount. It is further understood that similarly to the defatted soybean described above, the yuba contains daidzin and genistin in large amounts and daidzein and genistein which are aglycones thereof in small amounts.

Figure 4:
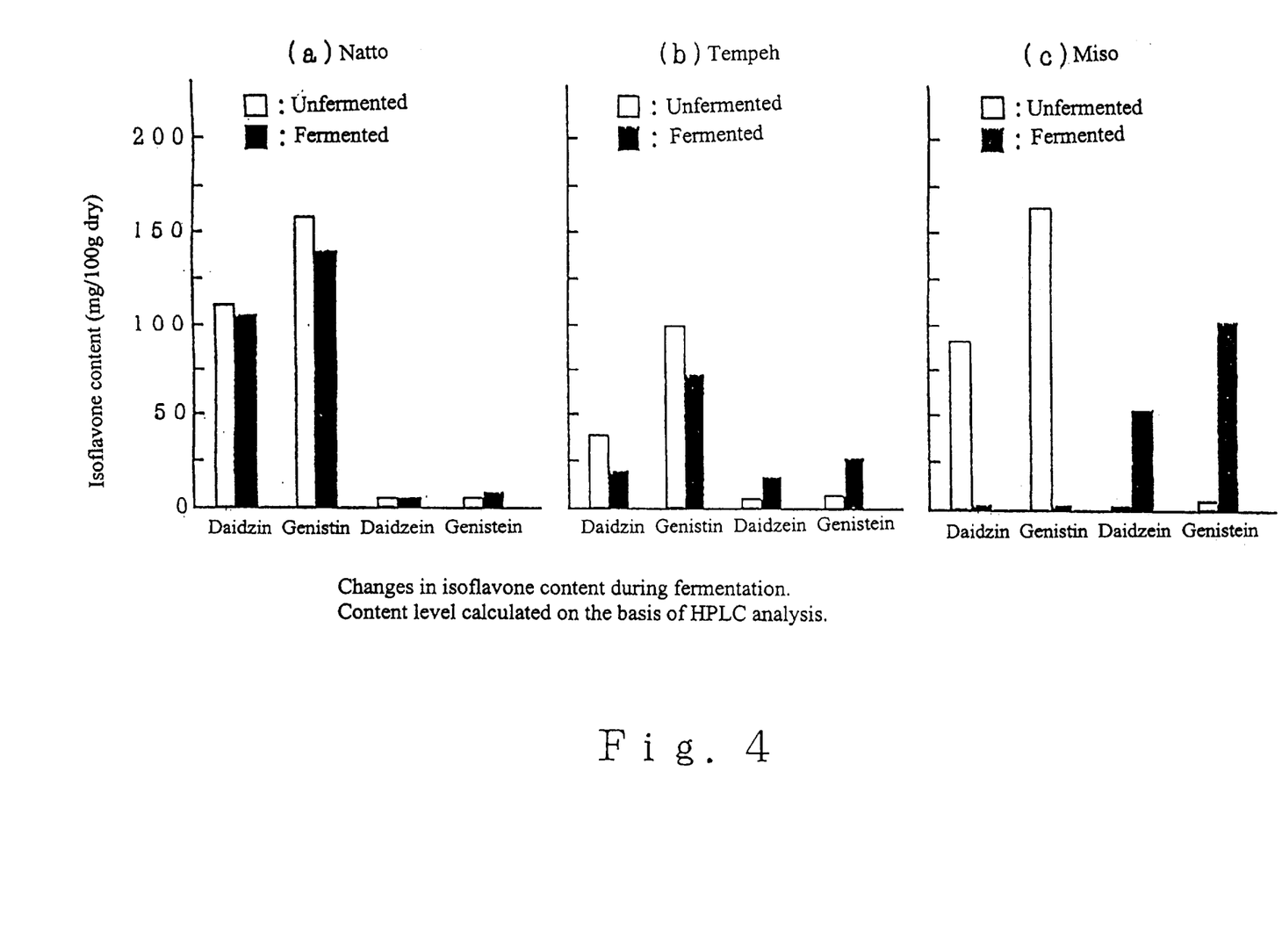
FIG. 4 is a characteristic diagram which shows changes in the isoflavone content during fermentation in natto, tempeh and miso.

Furthermore, when we look at soybean food products of other countries, "tempeh," which is a traditional fermented soybean food product of Indonesia, is a product prepared by fermentation using filiform bacteria of the genus Rhizopus following fermentation by lactic acid bacteria without the addition of salt. This product is used as a raw material for various types of side dishes; however, since absolutely no hydrolysis process is performed on the products produced by the koji preparation process following said koji preparation treatment as in the present invention, it has been reported together with the data shown in FIGS. 4(a) through 4(c) that the rate of aglyconization in which the isoflavone compounds daidzin and genistin contained in soybeans are converted into daidzein and genistein (which are aglycones from which the respective glycosides have been separated) is extremely low compared to that of the above-described miso, etc. (Esaki, H. et al.: ACS Symposium Series 546 "Food Phytochemical for Cancer Prevention I" (1994) 353–360). Accordingly, aglycones constituting health-promoting components cannot be produced more efficiently and in higher concentrations by means of the "tempeh".

With respect to a soybean miso (mame miso), a rice miso (kome miso), Daitokuji Soy nuggets (Daitokuji-natto: a Japanese fermented soy-food in the form of nuggets), dried-frozen tofu (Kori-tofu, tofu: a Japanese food made of soy milk curds) and yuba (yuba: a Japanese food made of a film which forms on a surface of thick soy milk when the soy milk is gently heated) as commercially available foods made from a pulse crop as a starting material, phytic acid contents were measured. The results are as shown in Table 3 below.

TABLE 3

| Units: mg/100 g | |
|---|---|
| | Phytic Acid |
| Soybean miso | Not detected |
| Rice miso | Not detected |
| Daitokuji natto | Not detected |
| Dried-frozen tofu | 506 |
| Yuba | 361 |

Detection limit: 5 mg/100 g

It is seen from this Table 3 that phytic acid is almost completely broken down in soybean miso, rice miso and Daitokuji natto, which are subjected to fermentation treatments. However, soybean miso, rice miso and Daitokuji natto have high salt concentrations, and cannot be eaten in large amounts. Furthermore, it is seen that the phytic acid content is large in the case of frozen tofu and dried tofu, so that myo-inositol cannot be digested and absorbed.

Furthermore, in regard to other pharmacological actions, soybeans in particular (among various types of beans) consist chiefly of protein, and miso and soy sauce are famous as food products in which this protein is broken down into peptides and amino acids by the protease of koji organisms. Moreover, in such miso and soy sauce, it is claimed that a chemical reaction (Maillard reaction) takes place with carbohydrates and fats which are components of the same soybeans as a result of a drop in the molecular weight of the protein, so that browning and fragrant aromas (aroma of ripening) are produced. In recent research concerning such Maillard reaction products, it has been reported that intermediate Amadori rearrangement products and brown melanoidin or AGE (advanced glycation end product), which are final products, are produced, and that these components are anti-mutagenic substances (Hiromich Kato: Miso no Kagaku to Gijutsu, Vol. 41, No. 2, 40–48 (1993)). However, the following problem arises: i e., miso and soy sauce are food products with a high salt content and cannot be eaten in large amounts.

If it were possible to ingest large amounts of a food product containing large amounts of products including health-promoting components with a superior pharmacological effect such as those described above, it would be possible to enjoy a diet exhibiting superior effects in terms of health maintenance in humans. Conventionally, however, there has been no food product which satisfies such a demand.

In particular, components which latently contain health-promoting components such as the above-described isoflavones, saponins or phytic acid, etc., either contain glycosides as in isoflavones and saponins, or form chelate bonds as in phytic acid. Accordingly, such components tend not to be absorbed by single-stomached animals including human beings or the gastrointestinal digestive tracts of animals; and hepatic function, etc., cannot be improved regardless of the amounts of such components that are ingested.

Conventionally, furthermore, it has been impossible to convert isoflavones, saponins or phytic acid, etc. into forms that are easily digested and absorbed.

The present invention has been made in light of the these points, and the object is to provide a product containing a health-promoting component that includes at least one member of the group consisting of liver function improving constituents, cardiac function improving constituents, anti-inflammatory constituents, antifat constituents, antioxidation consititents and antimutagen constituents; to provide applied products that contain the above-described product, as an ingredient, such as foods which can be ingested in a large amount, livestock feeds, diets of pets and precursory products for pharmaceutical preparations; and further to provide a process for readily preparing the above-described product in a large amount at a low cost.

Another object of the present invention is to provide a process for preparing a product that contains, in addition to the above-described health-promoting component, a health-promoting component which also contains large quantities of bacteria that have an intestine-regulating effect (hereafter referred to as "intestine-regulating bacteria") in single-stomached animals. Here, the term "single-stomached animals" refers to animals which do not have a ruminant stomach such as human beings, pets such as dogs and cats, etc., livestock such as horses and pigs, etc., and birds, etc.

In order to accomplish the object, the product of the present invention containing the health-promoting component claimed in claim 1 is characterized in that: the product contains a health-promoting component produced by inoculating koji mold on a pulse crop to effect koji preparation, and then hydrolyzing the products produced by this koji preparation treatment, and the product contains a health-promoting component consisting of intestine-regulating bacteria added to the beans and grown during the period extending from the inoculation of the koji mold to the completion of the hydrolysis.

Furthermore, the process of the present invention for preparing a product that contains the health-promoting component claimed in claim 6 is characterized in that: the health-promoting component is produced by inoculating koji mold on a pulse crop to effect koji preparation, and then hydrolyzing (through the addition of water) the products produced by this koji preparation treatment, and the product that contains the health-promoting component is produced by adding intestine-regulating bacteria which constitute a health-promoting component to the beans and growing the bacteria during the period extending from the inoculation of the koji mold to the completion of the hydrolysis.

The above-described intestine-regulating bacteria are characterized in that they are added at the same time as the inoculation of the koji mold and consist of lactic acid bacteria which have an intestine-regulating effect in single-stomached animals. These intestine-regulating bacteria, and especially lactic acid bacteria, have a good compatibility with the koji mold used in koji preparation, and also propagate very well on their own without interfering with the propagation of the koji mold, so that production efficiency is also superior.

More specifically, koji mold have the property of being able to coexist compatibly with lactic acid bacteria, etc. Accordingly, in the present invention, an effect in which koji mold and lactic acid bacteria are caused to be co-present on a substrate consisting of beans (via a process involving the co-presence and co-growth of koji mold and lactic acid bacteria) is utilized to produce a food product having an object of health maintenance of intestine-regulation functions, etc. in humans and animals.

Yogurt may be cited as an example of a healthy food product utilizing lactic acid bacteria; however, yogurt is not a food product which utilizes koji mold.

The fact that koji mold can co-exist and be co-grown compatibly with lactic acid bacteria, etc., has also been utilized in the past; however, this utilization has been limited to the production of refined sake, shochu, miso and soy sauce, etc., as fermented products, utilizing koji mold.

First, in refined sake, lactic acid bacteria are added in order to cause the growth of large quantities of only sake-refining yeast which has a strong activity in the initial stage. This process is called "yamahai-moto", a traditional Japanese term; here, lactic acid bacteria are naturally admixed and these lactic acid bacteria produce lactic acid, so that an action. which suppresses the propagation of organisms (film yeast, wild yeast, etc.) that are a problem in the manufacture of high-quality refined sake, is utilized. Today, a process in which lactic acid is added ("tokujo moto" or rapid fermentation) has also been developed.

Meanwhile, in the manufacture of sake, lactic acid bacteria known as "hiochii" bacteria which grow with a preference for alcohol cause changes such as cloudiness, an increase in acid and changes in fragrance, etc., and are therefore rather considered to be a problem. It has been found that such "hiochii" bacteria are lactic acid bacteria that require mevalonic acid. It has been confirmed that such mevalonic acid is caused to accumulate with the propagation of organisms in the koji preparation step by koji mold such as *Aspergillus oryzae*, etc. Incidentally, it is claimed that lactic acid bacteria that require this mevalonic acid commonly include bacteria that produce bacteriocin.

Furthermore, in miso and soy sauce, lactic acid bacteria are used as a countermeasure to inhibit the growth of undesirable organisms in the aging process.

Thus, products utilizing koji mold are respective products obtained via processes involving the co-presence and co-growth of koji mold and lactic acid bacteria or yeast. However, there has been no food product consisting of a fermented food having an object of health maintenance (e.g., intestine-regulating action, etc.) in humans and animals obtained by utilizing an effect which causes the co-presence and co-growth of koji mold and lactic acid bacteria on substrate grains as in the present invention.

The above-described health-promoting component produced by the koji preparation treatment and hydrolysis treatment are characterized so as to be comprised of at least one member of the group consisting of liver function improving constituents, cardiac function improving constituents, anti-inflammatory constituents, antifat constituents, antioxidation consititents and antimutagen constituents; and it is further characterized in that said component is formed so as to be absorbed by the digestive tract.

According to the process of the present invention, a health-promoting component can be produced in a product using beans as a raw material by means of a koji preparation treatment and a hydrolysis treatment. Furthermore, intestine-regulating bacteria which are added following the initiation of the koji preparation treatment but prior to the completion of the hydrolysis treatment can be propagated, so that the health-promoting component consisting of such intestine-regulating bacteria can also be included in large amounts.

In concrete terms, proteins, isoflavones, saponins and phytic acid, etc., are respectively converted into the health-promoting component such as peptides, isoflavone aglycones, saponin aglycones, myo-inositol and Maillard reaction products, etc., by performing a koji preparation treatment and a hydrolysis treatment on beans used as a raw material, and are thus converted into a state in which these components can be very easily absorbed by the digestive tracts of single-stomached animals, etc. Using the product of the present invention which has such a health-promoting component based on the above-described koji preparation treatment and hydrolysis treatment, health promotion by means of at least one member of the group consisting of liver function improving constituents, cardiac function improving constituents, anti-inflammatory constituents, antifat constituents, antioxidation consititents and antimutagen constituents can be accomplished very effectively.

In the present invention, furthermore, intestine-regulating bacteria which are added following the initiation of the koji preparation treatment but prior to the completion of the hydrolysis treatment can be propagated very favorably, so that a health-promoting component consisting of such intestine-regulating bacteria can be included in large amounts in the final product, and can thus be used for intestinal regulation in single-stomached animals.

In particular, if intestine-regulating bacteria are added simultaneously with the inoculation of koji mold, these intestine-regulating bacteria will be propagated in large amounts in the process up to the completion of hydrolysis, so that the propagation of other undesirable organisms can be inhibited.

Furthermore, by the use of lactic acid bacteria which have an intestine-regulation action in single-stomached animals as the above-described intestine-regulating bacteria, an intestine-regulating action can be reliably manifested in single-stomached animals, and the propagation of other undesirable bacteria can be reliably inhibited by the lactic acid bacteria, which are acid-producing bacteria.

The product thus prepared can be utilized directly, and it also can be utilized in applied products which use this product as a raw material, e. g., food products, livestock feeds, pet foods or drug raw materials, etc., thus being superior in terms of all-purpose utility. Miso and soy sauce are foods with a high salt content since salt is added following the koji preparation step, thus having less all-purpose utility; moreover, the aging period of such food products following the koji preparation step is extremely long, thus having problems in productivity. To the contrary, according to the present invention, the product is easy to manufacture and realizes a saving in costs.

Since the product and preparation process of the present invention are constructed and act as described above, a health-promoting component can be produced in a product using beans as a raw material, by means of a koji preparation treatment and a hydrolysis treatment. In concrete terms, peptides, isoflavones, saponins and phytic acid, etc. are respectively converted into a health-promoting component such as isoflavone aglycones, saponii aglycones, myo-inositol and Maillard reaction products, etc. and are thus converted into a state which can be very easily absorbed by the digestive tracts of single-stomached animals. In the present invention, furthermore, the intestine-regulating bacteria added following the initiation of the above-described koji preparation treatment but prior to the completion of the hydrolysis treatment propagate so that a health-promoting component consisting of such intestine-regulating bacteria can be included in the product in large amounts, thus making it possible to achieve an intestine-regulating effect in the intestines of single-stomached animals. By using the product of the present invention which contains such a health-promoting component, health promotion by means of at least one member of the group consisting of liver function improving constituents, cardiac function improving constituents, anti-inflammatory constituents, antifat constituents, antioxidation consititents and antimutagen constituents and components which have an intestine-regulating effect in single-stomached animals can be accomplished very effectively. This product can be used directly "as is", or the efficacy can be strengthened by extracting and concentrating the isoflavone aglycones, saponin aglycones, myo-inositol or Maillard reaction products, etc; in addition, this product can also be utilized in applied products which use this product as a raw material, e. g., food products, livestock feeds, pet foods or drug raw materials, etc. and is thus superior in terms of all-purpose utility. Furthermore, miso and soy sauce are foods with a high salt content, since salt is added following the koji preparation step, so that such food products lack all-purpose utility; moreover, the aging period of such food products following the koji preparation step is extremely long, so that there are problems in productivity. However, the product of the present invention is easy to manufacture at a low-cost.

BEST MODE TO CARRY OUT THE INVENTION

Below, embodiments of the present invention will be described with reference to the attached figures.

Figure 1:
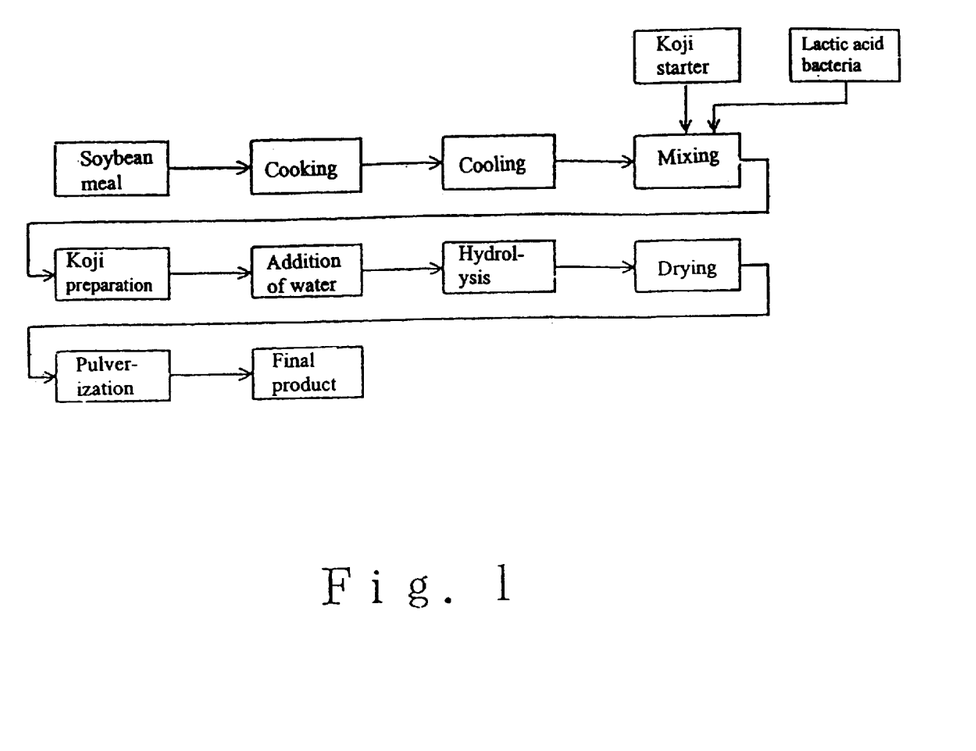
FIG. 1 is a process diagram which illustrates a first embodiment of the process of the present invention for preparing a product containing a health-promoting component.

FIG. 1 is a process diagram which illustrates one embodiment of the process of the present invention for preparing a product containing a health-promoting component, in which latent health-promoting components contained in soybean meal, a type of soybeans, are produced.

To describe the process according to FIG. 1, the soybean meal is first cooked. The propagation of koji mold is facilitated by this cooking. This cooking of the soybean meal may be performed either continuously or in a batch process according to the object of preparation, etc.

Then, when this cooking is completed, the soybean meal is temporarily cooled, and the moisture content in the soybean meal is adjusted to an amount (e.g., 40 wt %) that allows the propagation of koji mold.

In cases where defatted soybean meal, etc. is used as a raw material, this cooking process may be omitted.

The process of the present invention is performed as described below using soybean meal whose moisture content has thus been adjusted.

More specifically, koji starter consisting of koji mold is added at a prescribed weight ratio to the simple soybean meal following the completion of cooking; furthermore, lactic acid bacteria constituting a type of intestine-regulating bacteria are added, and these three ingredients are mixed until a uniform mixture is obtained.

Afterward, the mixture is placed in a koji preparation device and held for a prescribed period of time with the initial temperature set at approximately 28 to 30° C. Koji preparation is then performed by fermenting the soybean meal with a low moisture content of 40 wt % by means of koji mold until the enzymes required in order to convert the proteins, isoflavones, saponins and phytic acid, etc., contained in the soybean meal into respective health-promoting components such as peptide, isoflavone aglycones, saponin aglycones, myo-inositol and Maillard reaction products, etc., are produced.

In concrete terms, in the case of isoflavones and saponins, the respective glycosides are decomposed so that aglycones are produced. Furthermore, in the case of phytic acid, which is a compound in which phosphate groups are bonded to all of the hydroxy groups of myo-inositol, the above-described phosphate groups are dissociated by means of an enzyme that breaks down phytic acid, so that one or more of the compounds inositol pentaphosphate, inositol tetraphosphate, inositol triphosphate, inositol diphosphate, inositol monophosphate and inositol are produced.

With respect to such cases in which a health-promoting component is produced by this koji preparation step, a case will be described in which the glycosides of isoflavones and saponins are decomposed so that respective isoflavone aglycones and saponin aglycones are produced.

In this case, an enzyme known as β-glucosidase, which decomposes the glycosides of isoflavone compounds and is manufactured by koji mold as a result of the propagation of koji mold in the soybean meal, breaks down the glycosides of the isoflavone compounds in the soybean meal and thus produces isoflavone aglycones. Furthermore, an enzyme known as β-glucuronidase, which decomposes the glycosides of saponins and is manufactured by the koji mold, breaks down the glycosides of the saponins contained in the soybean meal and thus produces saponin aglycones.

The koji mold used in this koji preparation is koji mold that have long been used in Japanese fermented food products and tempeh; for example, koji mold from the genus Aspergillus and genus Rhizopus which are stable in food products, such as *Aspergillus usami, Aspergillus kawachii, Aspergillus awamori, Aspergillus saitoi, Aspergillus oryzae* and *Aspergillus niger*, etc. are desirable for use.

In regard to the fermentation time, the fermentation time is set at least 24 hours or longer in accordance with the type of koji mold used. It is desirable that the fermentation time be sufficient to cause thorough decomposition of the glycosides of the isoflavones and saponins in the soybean meal.

Figure 2:
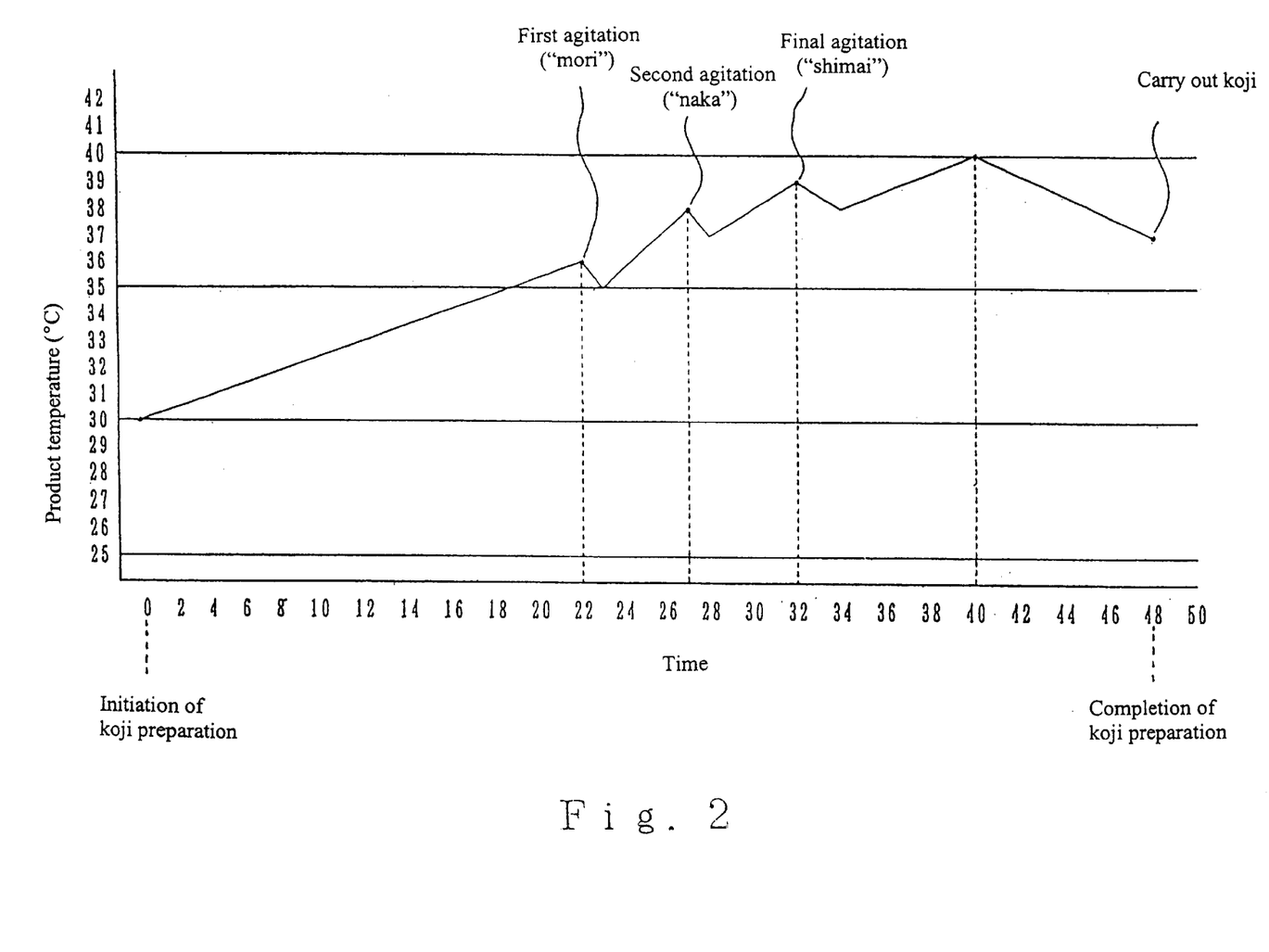
FIG. 2 is a graph which illustrates the temperature characteristics of the mixture accompanying the progression of koji preparation time in the present invention.

The temperature of the mixture in this koji preparation apparatus varies over time as shown for example in FIG. 2 as the manufacture of koji progresses. In particular, from the initiation of koji preparation until a state of "mori" (the first agitation) is reached after 22 hours, the temperature gradually rises. Then, when "mori" (the first agitation) is passed, the temperature drops slightly, and then again gradually rises until a state of "naka" (the second agitation) is reached after 27 hours. When the mixture in a state of "naka" (the second agitation) is agitated, the temperature drops slightly, and then again rises until a state of "shimai" (the final agitation) is reached after 32 hours. When the mixture in a state of "shimai" (the final agitation) is agitated, the temperature drops slightly, and then again nses until a time of 40 hours has elapsed. Afterward, the temperature gradually drops, and koji preparation is completed after 48 hours.

Under the above-described koji preparation conditions, the lactic acid bacteria (with an intestine-regulating effect in single-stomached animals) that are added simultaneously with the inoculation of the koji mold in the above-described koji preparation step propagate very favorably; and the multiplication of other undesirable organisms can be reliably suppressed. *Lactobacillus butgaricus* and *Streptococcus thermophilus*, etc., which are commonly used in yogurt in Europe, may be used as lactic acid bacterial agents.

Using microbiological nomenclature, *Bifidobacterium bifidum, Bifidobacterium infantis, Bifidobacterium longum, Enterococcus faecalis, Lactobacillus acidophilus, Lactobacillus casei, Lactococcus lactis* and *Pediococcus sp.*, etc., may be cited as examples of such lactic acid bacteria that have an intestine-regulating function in single-stomached animals.

The lactic acid bacteria used as such bacteria with an intestine-regulating function have good compatibility with the koji mold used in koji preparation, and show extremely good propagation themselves without hindering the propagation of the koji mold, so that the production efficiency is also superior.

Next, water is added to the product following the completion of koji preparation, and the product is maintained for a prescribed time in a state in which the temperature is elevated to a temperature of 30 to 65° C.; accordingly, the glycosides of the isoflavones and saponins contained in the soybean meal are sufficiently diminished by the decomposing actions of the β-glucosidase and β-glucuronidase contained in the product. As a result, hydrolysis is performed while aglycones of the isoflavones and saponins are produced.

In regard to the hydrolysis of the above-described proteins, it is desirable to use a hydrolysis time and hydrolysis temperature that are sufficient to cause a thorough diminishment of the glycosides of the isoflavones and saponins contained in the soybean meal in accordance with the type of koji mold used.

If this is done, organic acids will be produced in the initial stage of fermentation so that the propagation of undesirable organisms in the soybean meal is suppressed. Accordingly, there is no danger of secondary contamination, and a product using soybean meal as a raw material can be produced in large quantities.

Table 4 shows the contents of isoflavone compounds in 100 g of soybean meal in a case where untreated soybean meal were subjected to koji preparation for 48 hours at an initial temperature of 30° C., after which an amount of water equal to the weight of the product was added, and protein hydrolysis was performed for an additional 24 hours at 30° C.

TABLE 4

| Daidzin | Daidzein | Genistin | Genistein |
|---------|----------|----------|-----------|
| 25      | 74       | 53       | 59        |

(Units: mg/100 g)

According to this Table 4, the amounts of daidzein and genistein, which are aglycones of isoflavone compounds, were 74 mg and 59 mg, values that were respectively approximately 23 times and 14 times the values seen in the conventional example shown in FIG. 1; thus, the amounts of these compounds were greatly increased. It is seen from this that the amounts of daidzein and genistein produced can be further increased by performing hydrolysis for 24 hours or longer following the completion of koji preparation.

With the same object as Table 4, Table 5 shows the values before treatment and after treatment for other embodiments in which the treatment of the process of the present invention was performed on untreated soybean meal and separated soybean protein.

Describing the soybean meal first, the ratio of koji mold to raw material was selected so that 0.1 g of crudely refined white rice containing koji mold spores at the rate of $8 \times 10^7$ spores/g was added to 100 g of soybean meal constituting the raw material. Using this ratio of koji mold to raw material, untreated soybean meal was subjected to koji preparation. for 48 hours at an initial temperature of 30° C.; then, an amount of water equal to the weight of the product was added, and protein hydrolysis was performed for an additional. 48 hours at 50° C. The results obtained were as shown in Table 5.

Meanwhile, the above-described commercially marketed soybean protein used was FUJINIC 200 (commercial name) manufactured by Fuji Purina Protein Kabushiki kaisha. In this case, the ratio of koji mold to raw material was selected so that 0.1 g of crudely refined white rice containing koji mold spores at the rate of $8 \times 10^7$ spores/g was added to 100 g of commercially marketed soybean protein constituting the raw material. Using this ratio of koji mold to raw material, untreated commercially marketed soybean protein was subjected to koji preparation for 48 hours at an initial temperature of 30° C.; then, an amount of water equal to the weight of the product was added, and protein hydrolysis was performed for an additional 48 hours at 50° C. The results obtained were as shown in Table 5.

TABLE 5

|           | Soybean meal | | Commercially marketed soybean protein | |
|-----------|--------|--------------|--------|-------|
|           | Before | After        | Before | After |
| Daidzin   | 100    | Not detected | 90     | 1.0   |
| Daidzein  | 3.2    | 70           | 5.3    | 100   |
| Genistin  | 120    | 1.3          | 120    | 3.3   |
| Genistein | 4.2    | 64           | 4.4    | 94    |

(Units: mg/100 g)

According to this Table 5, the amounts of daidzein and genistein, which are aglycones of isoflavone compounds, in the case of soybean meal, were 70 mg and 64 mg, which were respectively approximately 22 times and 15 times the values measured prior to treatment; thus, the amounts of these compounds were greatly increased. Furthermore, daidzin, which is an isoflavone compound with glycosides, was decomposed until it could no longer be detected, and genistin was also greatly diminished to a value of 1.3 mg.

Furthermore, in the case of commercially marketed soybean protein as well, the amounts of daidzein and genistein, which are aglycones of isoflavone compounds, were 100 mg and 94 mg, which were respectively approximately 19 times and 21 times the values measured prior to treatment; thus, the amounts of these compounds were greatly increased. Furthermore, daidzin and genistin, which are isoflavone compounds with glycosides, were greatly diminished to 1.0 mg and 1.3 mg, respectively.

Thus, according to the present invention, aglycones which have a high pharmacological effect among isoflavones and saponins, etc. contained in soybeans can be manufactured with an extremely high production efficiency.

Next, the manufacture of a product, in which free myo-inositol is produced as a health-promoting component and phytic acid contained in soybean meal is removed, will be described.

In this case, enzymes known as phytase and phosphatadase which decompose phytic acid and are manufactured by koji mold as a result of the propagation of such koji mold in soybean meal decompose and remove the phytic acid contained in soybean meal.

More specifically, from phytic acid, which is a compound in which phosphate groups are bonded to all of the hydroxy groups of myo-inositol, the above-described phosphate groups are dissociated by means of an enzyme that breaks down phytic acid, so that one or more of the compounds inositol pentaphosphate, inositol tetraphosphate, inositol triphosphate, inositol diphosphate, inositol monophosphate and inositol are produced, thus removing the phytic acid.

The koji mold used in this koji preparation is koji mold that have long been used in Japanese fermented food products and tempeh; for example, koji mold from the genus Aspergillus and genus Rhizopus which are safe as food products and which have a high phytase potency and phosphatadase potency, such as *Aspergillus usamii, Aspergillus kawachi, Aspergillus awamori, Aspergillus saitoi, Aspergillus oryzae* and *Aspergillus niger*, etc., are desirable for use.

In regard to the fermentation time, the fermentation time is set at least 24 hours or longer in accordance with the type of koji mold used; and it is desirable that the fermentation time be sufficient to cause thorough removal of the phytic acid contained in the soybean meal.

In the subsequent hydrolysis process and decomposition process, water is added to the product following the completion of koji preparation, and the product is then maintained for a prescribed period of time in a state in which the product is heated to a temperature of 30 to 55° C. As a result, the phytic acid contained in the soybean meal is sufficiently diminished by the decomposing actions of the phytase and phosphatadase contained in the product, and hydrolysis is performed.

In regard to this hydrolysis, it is desirable that the hydrolysis time and hydrolysis temperature used be sufficient to cause thorough removal of the phytic acid contained in the soybean meal in accordance with the type of koji mold used.

Furthermore, the removal of phytic acid is accomplished by liberating at least one phosphate group from the phytic acid, which consists of inositol hexaphosphate. The number of phosphate groups liberated may be determined in accordance with the desired health-promoting action. In this case, the number of phosphate groups liberated from the phytic acid may be controlled by adjusting the fermentation time, hydrolysis time and hydrolysis temperature in accordance with the type, state, characteristics and quantity of the beans, the type, state, characteristics and quantity of the koji mold, and the type and characteristics, etc. of the product.

Table 6 shows the phytic acid content in 100 g of soybean meal for untreated soybean meal, soybean meal A and B which were subjected to koji preparation for 48 hours at an initial temperature of 30° C. using two types of shochu malt (*Aspergillus niger* and *Aspergillus awamori*), and which were then subjected to hydrolysis for an additional 24 hours at 30° C. following the addition of an equal weight of water to the respective products, and soybean meal which was subjected to a conventional alcohol cleaning treatment.

TABLE 6

| Object soybean meal | Phytic acid content (mg/100 g) |
| --- | --- |
| Untreated soybean meal | 999 (mg/100 g) |
| Shochu malt treatment A | Not detected |
| Shochu malt treatment B | Not detected |
| Alcohol-cleaned soybean meal | 1150 (mg/160 g) |

(Detection limit: 5 mg/100 g)

According to this Table 6, the phytic acid content in untreated soybean meal was 999 mg, or approximately 1%, while the phytic acid contents of soybean meal A and B, which were subjected to a shochu malt treatment according to the process of the present invention, and which were then subjected to protein hydrolysis for an additional 24 hours at 30° C. following the addition of an equal weight of water to the respective products, were diminished to a point where said phytic acid contents could not be detected, i.e., to a point where all of the phytic acid was decomposed.

On the other hand, the phytic acid content in the soybean meal subjected to a conventional alcohol cleaning treatment was 1150 mg, and thus showed no decrease at all.

Thus, according to the present invention, it is possible to achieve a great reduction or almost complete elimination of phytic acid in soybeans.

Next, the propagation of lactic acid bacteria (which are a type of intestine-regulating bacteria) in the present invention will be described.

In the present embodiment, lactic acid bacteria are added simultaneously with the inoculation of the koji mold; accordingly, these lactic acid bacteria propagate in large quantities in the process leading up to the completion of hydrolysis. Furthermore, since lactic acid bacteria are acid-producing bacteria, the propagation of other undesirable organisms can be reliably suppressed by the acid produced; and the product obtained has a good fragrance and taste. Lactic acid bacteria which have an intestine-regulating action in single-stomached animals are contained in large quantities in the product thus produced, and the product also contains bacteriocin produced by the lactic acid bacteria; accordingly, an intestine-regulating action can be reliably manifested in single-stomached animals when such animals ingest this product.

To describe this further, using defatted soybeans as a raw material, miso koji mold (*Aspergillus oryzae*) and lactic acid bacteria (*Lactococcus lactis* subsp. *lactis*) were mixed with the soybeans in such proportions that 0.1 g of crudely refined white rice containing koji mold spores of the miso koji mold at the rate of $8 \times 10^7$ spores/g was added to 100 g of the raw-material defatted soybeans, and the number of lactic acid bacteria added was on the order of $10^3$ colony forming unit (cfu)/g. Then, koji preparation was performed for 48 hours at an initial temperature of 30° C., and protein hydrolysis was performed for an additional 41 hours at 50° C. following the addition of an equal weight of water to the product. In this case, the number of lactic acid bacteria in respective products dried by a hot air draft immediately after the completion of koji preparation (koji product), and following 13 hours, 24 hours, 30 hours and 41 hours of hydrolysis, was investigated. Furthermore, 0.1 g of each of the products was added to 100 ml of milk and separately to 100 ml of a suspension prepared by dissolving 16 g of commercially marketed skim milk in 140 ml of water, and the pH was investigated immediately after addition and after 18 hours at 40° C. The results obtained are shown in Table 7.

TABLE 7

|  | Number of lactic acid bacteria | Milk | | Defatted powdered milk | |
| --- | --- | --- | --- | --- | --- |
|  |  | After 0 hours | After 18 hours | After 0 hours | After 18 hours |
| Koji product | $(1.2 \times 10^7)$ | 6.77 | 4.73 | 6.65 | 4.80 |
| After 13 hours of hydrolysis | $3.4 \times 10^9$ | 6.78 | 4.54 | 6.63 | 4.54 |
| After 24 hours of hydrolysis | $2.9 \times ^9$ | 6.77 | 4.54 | 6.64 | 4.57 |
| After 30 hours of hydrolysis | $3.1 \times 10^9$ | 6.76 | 4.55 | 6.63 | 4.54 |
| After 41 hours of hydrolysis | $2.2 \times 10^9$ | 6.76 | 4.52 | 6.63 | 4.55 |

According to this Table 7, the lactic acid bacteria were greatly increased from the order of $10^3$ colony forming unit (cfu)/g to the order of $10^7$ colony forming unit (cfu)/g in the koji preparation step and were further greatly increased to the order of $10^9$ colony forming unit (cfu)/g in the subsequent hydrolysis process. Furthermore, it is also seen that the compatibility of the miso koji mold (*Aspergillus oryzae*) and the lactic acid bacteria (*Lactococcus lactis* subsp. *lactis*) is good. Moreover, since no ventilation was performed in the hydrolysis process, even the anaerobic lactic acid bacteria showed considerable growth. When this concentration on the order of $10^9$ colony forming unit (cfu)/g was reached, no undesirable organisms recognized at the time of completion of the koji preparation step could be confirmed. The amount of lactic acid following hydrolysis was increased to a sufficient number; furthermore, it may be said that the propagation of undesirable aerobic organisms was reliably suppressed in the environment that was present during hydrolysis, and that the propagation of undesirable organisms was also reliably suppressed as a result of the action shown by *Lactococcus lactis* subsp. *lactis* in producing bacteriocin (see Gross, E. and Morell, J. L.: J. Am. Chem. Soc., 93, 4634–4635 (1971)). Furthermore, in the milk and skim milk suspensions containing 0.1 g of the respective samples, the pH was caused to drop from approximately 6.5 to approximately 4.5 after 18 hours had passed (at 40° C.) from the time of addition; thus, it is seen that the lactic acid bacteria showed further active propagation.

In regard to the timing of the addition of the lactic acid bacteria, these bacteria may be added at any time from the initiation of the koji preparation treatment to a point just prior to the completion of hydrolysis; however, it is desirable to insure a time that allows the prescribed propagation of the lactic acid bacteria.

In cases where the product containing a health-promoting component manufactured by completing a solid culture treatment in the manner described above is used in, for instance, food products, etc., the manufactured product can be used "as is" or can be formed as a final product by being dried and pulverized as shown in FIG. 1. In the present embodiment, lactic acid bacteria are used; accordingly, if these lactic acid bacteria are obligate anaerobes, it is desirable that the bacteria be dried by a freeze-drying method so that the lactic acid bacteria are not killed. On the other hand, in cases where the lactic acid bacteria are facultative anaerobes, drying by means of hot air draft drying at a low drying temperature may be used besides the above-described freeze-drying method.

Next, the product of the present invention which contains a health-promoting component will be described.

The product of the present invention includes a direct product that uses beans as raw materials and an applied product which uses such a direct product as a raw material (inclusive of cases where such a direct product is used as a portion of the raw material). For example such products include food products, livestock feeds, pet foods and drug raw materials, etc.

The product according to the process of the present invention using beans as a raw material can be manufactured without adding salt; accordingly, a food product with an extremely low salt content is obtained, so that large quantities of this product can be eaten when the product is used as a foodstuff.

Furthermore, a health-promoting component such as peptides, isoflavonle aglycones, saponin aglycones, myo-inositol and Maillard reaction products, etc., as well as a health-promoting component consisting of lactic acid bacteria, which are one type of intestine-regulating bacteria, and bacteriocin, which is a product of such bacteria, are contained in such food products.

Among the above-described health-promoting component, the components other than lactic acid bacteria can be very easily absorbed by the digestive tracts of single-stomached animals, etc. Furthermore, as described above, these health-promoting components comprise at least one member of the group consisting of liver function improving constituents, cardiac function improving constituents, anti-inflammatory constituents, antifat constituents, antioxidation consititents and antimutagen constituents; accordingly, a diet exhibiting superior effects in terms of health maintenance in humans can be enjoyed.

Furthermore, the lactic acid bacteria included in the health-promoting component have an intestine-regulating action in the intestines of single-stomached animals; accordingly, in cases where the intestine-regulating function is already good, this intestine-regulating function can be improved even further; and in cases where the intestine-regulating function is poor, this intestine-regulating function can be recovered, thus contributing to the maintenance and promotion of health in single-stomached animals.

For example, in regard to food products according to the product of the present invention, if this product is formed into configurations such as biscuits or cakes, etc., which can easily be eaten by humans, or if the product is formed "as is" (without being heated) into a drink such as a yogurt flavored drink or cocoa flavored drink, etc., which can easily be imbibed by humans, then, when the food product is eaten or imbibed, a health-promoting component which is superior in terms of a hepatic, function strengthening action, a cardiac function strengthening action, an anti-inflammatory action, a slenderizing action, an antioxidant action, an anti-mutagenic action and an intestine-regulating action, etc., can be ingested at the same time. In particular, if biscuits are eaten so that the daily ingestion requirement considered necessary in order to obtain the above-described health-promoting actions is satisfied, such ingestion alone is useful in preventing illness.

According to the preparation process of the present invention, live koji mold are grown, and aglycones which have a high pharmacological effect among isoflavones and saponins contained in beans are manufactured at an extremely high production rate; furthermore, the phytic acid contained in the beans is removed, and proteins are hydrolyzed. Therefore, aglycones can easily be produced and phytic acid can easily be removed in the case of solid beans; moreover, the manufacturing process is simple, and manufacturing costs are low.

Furthermore, in the preparation process of the present invention, a conventional koji preparation apparatus can be utilized "as is." There is no particular need to manufacture production base equipment. Thus, the present invention has high all-purpose utility.

EXAMPLES

The health-promoting action of the product of the present invention will be described below in terms of concrete practical examples of application.

Example 1

In the present practical example, a comparison of intestine-regulating action was made between an ordinary feed for suckling piglets, and feeds prepared by adding fermented defatted soybeans manufactured by the process of the present invention or plasma protein to the same ordinary feed.

Experimental Methods (1) Test Feeds

The respective feeds used were the base feed (control group) shown in Table 8 below, which was used as a feed for suckling piglets, a feed (test group) prepared by adding fermented defatted soybeans prepared by the process of the present invention to the base feed at a rate of 4%, and a feed (comparative group) prepared by adding plasma protein to the same base feed at a rate of 1.8%, with the crude protein contents being adjusted so that said contents were equal.

TABLE 8

Indicated components of base feed and names of raw materials, etc.

| Type of feed | Feed for suckling piglets (used during artificial suckling of piglets) | |
| --- | --- | --- |
| Indicated components | | |
| Crude protein | 22.0% or greater | |
| Crude fat | 3.0% or greater | |
| Crude fiber | 2.0% or less | |
| Crude ash content | 6.5% or less | |
| Calcium | 0.65% or greater | |
| Phosphorus | 0.50% or greater | |
| TDN | 84.0% or greater | |
| DCP | 20.0% or greater | |
| Names of raw materials, etc. | | |
| Classification of raw materials | Amount added | Name of raw material[1] |
| Grains | 46% | Powdered wheat, bread crumbs, dextrin, (soybean flour)[2] |
| Feeds consisting of | 32% | Skim milk, fish meal, (dried |

TABLE 8-continued

Indicated components of base feed and names of raw materials, etc.

| Type of feed | Feed for suckling piglets (used during artificial suckling of piglets) | |
| --- | --- | --- |
| animal substances | | whey) |
| Vegetable oils and lees | 3% | Concentrated soybean protein, potato protein |
| Other | 19% | Sugar, glucose, animal oils plasma protein, bread yeast, calcium phosphate, bacillus toyoi bacteria, fructooligosaccharides, silicic acid, citric acid, tartaric acid, lactic acid, malic acid, (calcium carbonate), (betaine), (salt) |
| Feed additives | | |
| Avilamycin (good's name) | | 40 g potency/ton |
| Morantel citrate | | 30 g/ton |
| Colistin sulfate | | 40 g potency/ton |

Notes)
[1] Raw material names are listed substantially in the order of amount added
[2] Raw materials shown in parentheses may be omitted in some cases depending on the raw material conditions, etc.

(2) Test Animals

26 WL×D hybrids (13 males and 13 females) were used as suckling piglets. The average body weight for all of the animals at the initiation of testing was 8.0 kg, and the average age was approximately 26 days.

(3) Test Methods

Inside a concrete pig shed with a natural ventilation system, the animals of the control group, test group and comparative group were placed in 190 cm×125 cm×75 cm all-drain board cages, with 6 animals to each cage so that the body weights were equal. Each group was raised for two weeks with free feeding and watering allowed. Each week, the body weights of the animals and the amounts of feed ingested were measured, and the body weight increase and feed requirements were determined from these values. The results are shown in Table 9. The health conditions of the piglets were also observed daily.

TABLE 9

Body weight, weight increase, amount of feed ingested and feed requirements.

| Numbers of animals | Control group 6 | Comparative group 6 | Test group 4 |
| --- | --- | --- | --- |
| Body weight (kg). | | | |
| After 0 days | 8.3 ± 0.8(100) | 8.3 ± 0.9(100) | 8.2 ± 0.8(98) |
| After 7 days | 10.2 ± 1.3(100) | 10.4 ± 1.2(103) | 10.7 ± 0.9(105) |
| After 14 days | 14.3 ± 1.7(100) | 14.5 ± 1.5(102) | 15.5 ± 1.0(109) |
| Increase in body weight (g/day/animal) | | | |
| After 0 to 7 days | 267 ± 102(100) | 300 ± 131(112) | 365 ± 88(137) |
| After 7 to 14 days | 587 ± 73(100) | 586 ± 68(100) | 688 ± 21(117) |
| After 0 to 14 days | 427 ± 86(100) | 443 ± 91(104) | 526 ± 42(125) |
| Amount of feed ingested (g/day/animal) | | | |
| After 0 to 7 days | 366(100) | 376(103) | 398(109) |
| After 7 to 14 days | 742(100) | 851(115) | 991(134) |
| After 0 to 14 days | 554(100) | 613(111) | 679(123) |

TABLE 9-continued

Body weight, weight increase, amount of feed ingested and feed requirements.

| Numbers of animals | Control group 6 | Comparative group 6 | Test group 4 |
|---|---|---|---|
| Feed requirement | | | |
| After 0 to 7 days | 1.37(100) | 1.25(92) | 1.09(80) |
| After 7 to 14 days | 1.26(100) | 1.45(115) | 1.44(114) |
| After 0 to 14 days | 1.30(100) | 1.39(107) | 1.29(99) |

Notes)
Mean value ± standard deviation (n − 1)
Numerals in parentheses are indices with the value for the control group taken as 100.

There was no diarrhea in any of the groups, and no deficiencies in body tone appeared. As shown in Table 9, the weight increase in the period from 0 to 14 days, during which the health conditions of the piglets appeared normal, was 25% higher in the test group than in the control group. This tendency appeared. in the first week following the initiation of testing, with the increase in body weight during the period of 0 to 7 days being 37% higher in the test group than in the control group. However, this difference was not significant. The weight increase during the period of 7 to 14 days was 17% higher in the test group than in the control group, and this difference was significant ($p<0.05$). In the comparative group in which plasma protein was added, the weight increase during the period of 0 to 14 days was only 4% higher than in the control group, so that no great effect was observed. Since no great increase in body weight was observed even in the case of a feed prepared by adding ordinary untreated defatted soybeans to the base feed, the results suggested that fermented defatted soybeans manufactured by the process of the present invention did not constitute a minus factor in terms of digestive absorption in young single-stomached animals such as piglets, etc., but rather showed a large plus factor, i.e., the presence of an intestine-regulating action.

Example 2

In this practical example, an experiment was conducted concerning the amount of a hepatic drug metabolizing enzyme (amount of cytochrome P-450) in respective feeds using fermented defatted soybeans manufactured according to the process of the present invention, untreated defatted soybeans and casein as protein sources.

Experimental Methods

Male mice of std:ddy at an age of 4 weeks and with a body weight of approximately 20 g (according to Nippon SLC) were raised for 7 days on a commercially marketed solid feed (MF manufactured by Oriental Kobo (yeast) Kabushiki Kaisha) in order to acclimatize the animals to the raising environment. Afterward, the animals were divided into three groups as shown in Table 10 below, i.e., a casein group (8 animals) using casein as a feed, a fermented defatted soybean group (8 animals) using fermented defatted soybeans manufactured by the process of the present invention as a feed, and an untreated defatted soybean group (8 animals) using unfermented defatted soybeans as a feed. These animals were raised for 4 weeks; on the final day of raising, the animals were killed by decapitation, and the livers were excised.

TABLE 10

Compositions of test feeds.

| Component | Casein (g/kg) | Fermented defatted soybeans (g/kg) | Untreated defatted soybeans (g/kg) |
|---|---|---|---|
| Casein | 200 | — | — |
| Fermented defatted soybeans | — | 325 | — |
| Untreated defatted soybeans | — | — | 365 |
| Mineral mixture | 35 | 35 | 35 |
| Vitamin mixture | 10 | 10 | 10 |
| Corn oil | 50 | 50 | 50 |
| Soybean fiber | 16 | — | 8 |
| Sucrose | 200 | 200 | 200 |
| α-cone starch | 489 | 380 | 332 |

(1) Preparation of Hepatic Microsomes

The livers excised as described above were immersed in an ice-cooled 0.15 M KCl solution, and excess blood was washed away. Afterward, a 0.1 M tris-hydrochloric acid buffer A (pH 7.4) was added, and a homogenate was prepared using a homogenizer. This homogenate was centrifugally separated (9000*G, 15 minutes, 4° C.), and the supernatant was collected. This supernatant was again centrifugally separated (105,000*G, 90 minutes, 4° C.), and the pellets thus obtained were suspended in a 0.1 M tris-hydrochloric acid buffer B (pH 7.4), thus producing hepatic microsome samples.

(2) Measurement of Protein Concentration

Measurements were performed using bovine serum albumin as a standard according to the method of Lowry (O. H. Lowry et al.: J. Biol. Chem., 193, 265, 1951).

(3) Measurement of Amount of Cytochrome P-450

Measurements were performed using the Method of Omura and Sato (T. Omura, R. Sato, J. Biol. Chem., 239, 2370, 1964).

As shown in Table 11 below, the measurement results were as follows: i.e., the amount of cytochrome P-450 was significantly lowest in the casein feed group. When the fermented defatted soybean group and the untreated defatted soybean group were compared, an increase in the amount of cytochrome P-450 was observed in the fermented defatted soybean group. It can be seen that this probably suggests that the amount of cytochrome P-450 in a dose-dependent manner with isoflavone aglycones. In other words, if the three test feeds are compared, it is seen that the fermented defatted soybeans manufactured by the process of the present invention cause the greatest increase (with a significant difference) in the amount of cytochrome P-450 (which is a hepatic drug metabolizing enzyme). Furthermore, cytochrome P-450 II also contributes to the promotion of metabolism in Practical Examples 3 and 4 described below; thus, it can be seen that fermented defatted soybean manufactured by the process of the present invention cause a significant increase in the promotion of metabolism.

TABLE 11

Effects of fermented deffatted soybeans on microsome protein levels and cytochrome P-450 level in hepatic microsomes.

| Feed | Liver weight (g) | Microsome protein (mg/g liver) |
|---|---|---|
| Casein | 2.07 ± 0.08[b] | 23.0 ± 1.0[a] |
| Fermented defatted soybeans | 1.99 ± 0.11[ab] | 25.2 ± 1.1[a] |
| Untreated defatted soybeans | 1.78 ± 0.08[a] | 26.1 ± 2.1[a] |
| Feed | Cytochrome P-450 (nmol/mg protein) | Cytochrome P-450 (nmol/g liver) |
| Casein | 0.42 ± 0.04[a] | 9.7 ± 1.2[a] |
| Fermented defatted soybeans | 0.92 ± 0.05[c] | 23.4 ± 2.1[c] |
| Untreated defatted soybeans | 0.65 ± 0.03[b] | 17.1 ± 1.8[b] |

Notes)
Mean value ± standard deviation (n = 8)
Mean values in vertical rows which do not have the same characters show significant differences (P < 0.05)
Testing for significant differences was accomplished by Duncan's multiple range test.

Example 3

In the present practical example, a feed using unfermented defatted soybeans as a raw material and a feed using fermented defatted soybeans manufactured by the process of the present invention as a raw material were compared with respect to the rate of acetaldehyde metabolism (in connection with the strengthening of hepatic function).

Experimental Methods

Using 15 ddy male mice with a body weight of approximately 20 g in each test group, the unfermented defatted soybean feed and the fermented defatted soybean feed which was manufactured by the process of the present invention, both shown in Table 12 below, were given to the mice for four weeks. Afterward, a 5% acetaldehyde suspension (suspended in distilled water) was injected into the abdominal cavity of each animal at the rate of 10 ml per kg of body weight. The time in a coma (from the onset of coma to re-awakening) was then measured.

TABLE 12

Experimental feeds

| | Unfermented defatted soybean feed (g/kg) | Fermented defatted soybean feed (g/kg) |
|---|---|---|
| Unfermented defatted soybean feed | 402 | — |
| Fermented defatted soybean feed | — | 359 |
| Corn oil | 50 | 50 |
| Vitamin mixture | 10 | 10 |
| Mineral mixture | 35 | 35 |
| Cellulose | 12 | — |
| α-corn starch | 291 | 346 |
| Sucrose | 200 | 200 |

As shown in Table 13 below, the measurement results indicate that the coma time was long, i.e., approximately 96 minutes, in the case of the group receiving the unfermented defatted soybean feed; on the other hand, the coma time was approximately 71 minutes, shortened by approximately 25 minutes, in the case of the group receiving the fermented defatted soybean feed manufactured by the process of the present invention. Thus, the product of the present invention can accelerate the rate of acetaldehyde metabolism and is thus able to prevent hangovers and deleterious after-effects of alcohol, and to strengthen hepatic function.

TABLE 13

Effect on coma time caused by acetaldehyde administration

| | Coma time (minutes) |
|---|---|
| Unfermented defatted soybean feed (n = 15) | 96 ± 9[a] |
| Fermented defatted soybean feed (n = 15) | 71 ± 7[b] |

Example 4

In the present practical example, on the basis of the effect of shortening acetaldehyde coma time observed in the fermented defatted soybeans in the above-described Practical Example 3, the effects of various types of protein sources (including fermented defatted soybeans manufactured by the process of the present invention) on acute acetaldehyde toxicity were compared.

Experimental Methods

Using 14 ddy male mice with a body weight of approximately 20 g in each group, the feeds shown in Table 14 below, i.e., an unfermented defatted soybean feed, a fermented defatted soybean feed manufactured by the process of the present invention, casein, egg white and gluten, were given to the mice for four weeks. Afterward, a 10% acetaldehyde suspension (suspended in distilled water) was injected into the abdominal cavity of each animal at the rate of 10 ml per kg of body weight, and the survival rate was measured.

TABLE 14

Protein source in feed (survival rate)

| | Fermented defatted soybeans | Untreated defatted soybeans | Casein | Egg white | Gluten |
|---|---|---|---|---|---|
| Same day | 11/14 (79%) | 10/14 (71%) | 8/14 (57%) | 5/14 (36%) | 2/14 (14%) |
| First day | 11/14 (79%) | 9/14 (64%) | 8/14 (57%) | 5/14 (36%) | 0/14 (0%) |
| Second day | 8/14 (57%) | 6/14 (43%) | 7/14 (50%) | 4/14 (29%) | 0/14 (0%) |
| Third day | 8/14 (57%) | 4/14 (29%) | 7/14 (50%) | 3/14 (21%) | 0/14 (0%) |
| Fourth day | 6/14 (43%) | 3/14 (21%) | 5/14 (36%) | 3/14 (21%) | 0/14 (0%) |
| Fifth day | 6/14 (43%) | 3/14 (21%) | 4/14 (29%) | 3/14 (21%) | 0/14 (0%) |

It was confirmed from these measurement results that mice fed with a fermented defatted soybean feed manufactured by the process of the present invention as a protein source had a higher survival rate than mice fed with an unfermented defatted soybean feed, casein, egg white or gluten as a protein source. Thus, it was confirmed that a capacity to break down acetaldehyde can be obtained by administering the fermented defatted soybean feed manufactured by the process of the present invention. In other words, it appears that there was an effect that increased the activity of aldehyde dehydrogenase, which is a second-phase detoxifying enzyme. It appears that this function is an action obtained by means of a product in which defatted soybeans are subjected to koji preparation using koji mold and are then hydrolyzed, so that components in the soybeans are changed by some type of enzyme.

Example 5

In this practical example, an evaluation of antioxidant action was performed by means of an AOM test, using products manufactured by the process of the present invention along with other substances as specimens. The results obtained are shown in FIG. 3.

Here, the products of the present invention that were used as specimens were a 0.1% ethanol extract of fermented and extracted soybean protein, and a 0.5% ethanol extract of fermented and extracted soybean protein. Furthermore, the other specimens used were an untreated extracted soybean protein (no additives), a 0.1% ethanol extract of untreated extracted soybean protein, a 0.1% ethanol extract of koji mold, and a 0.1% extract of 98% α-tocopherol.

The AOM test performed here is a test in which the respective specimens are added to lard, after which the resulting mixtures are heated to 90° C., and the peroxide value (POV) is measured over time.

Figure 3:
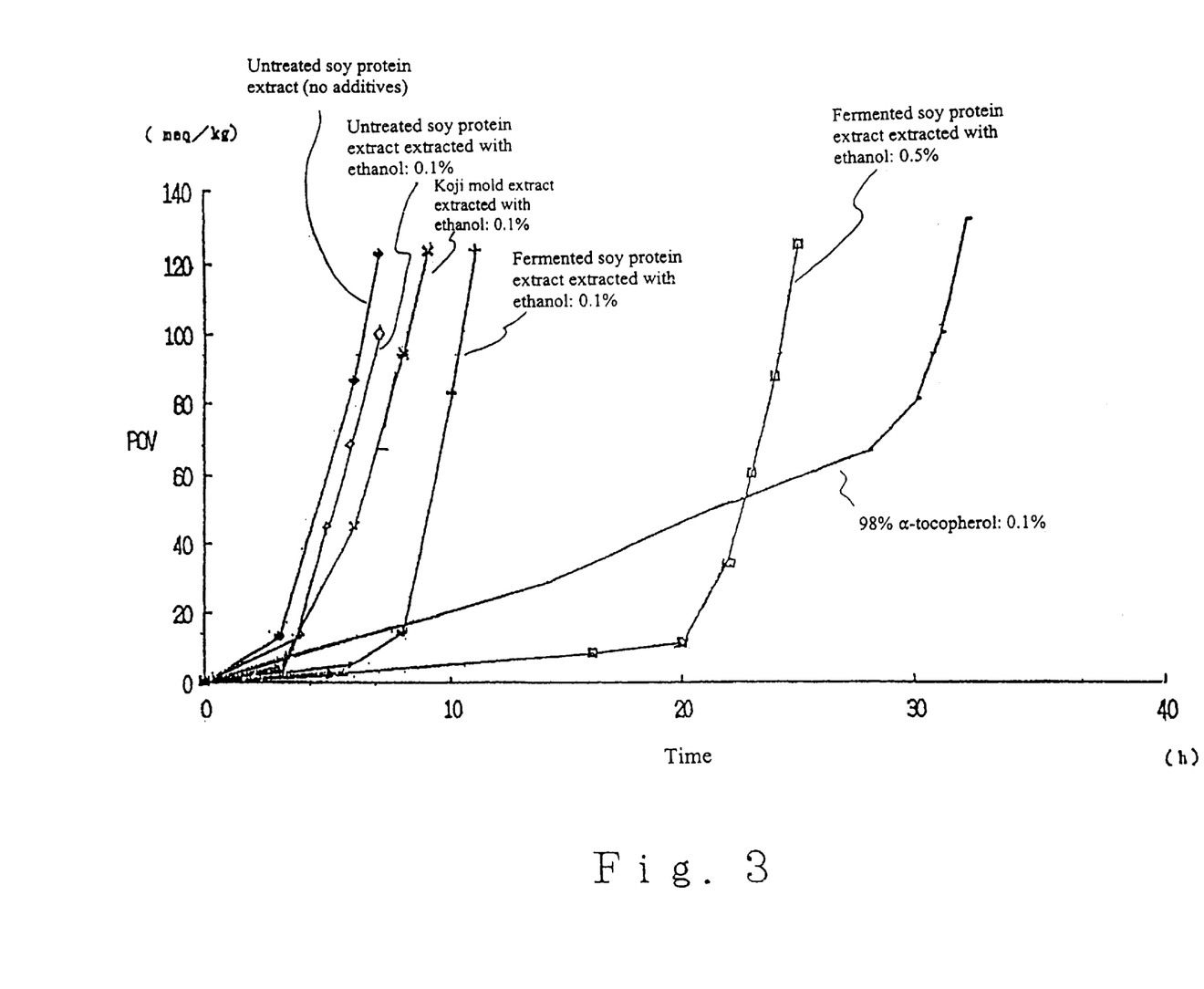
FIG. 3 is a characteristic diagram obtained by means of an AOM test in cases where a product prepared by the process of the present invention and other substances were used as samples.

It is seen from the results in FIG. 3 that the 0.1% ethanol extract of fermented and extracted soybean protein and 0.5% ethanol extract of fermented and extracted soybean protein constituting products of the present invention required a long time for the peroxide value (POV) to become elevated compared to untreated extracted soybean protein and were thus superior in terms of antioxidant action.

Thus, the product of the present invention has an antioxidant action similar to that of α-tocopherol and can suppress the oxidation of oil by being added in small amounts to dishes using large amounts of oil, etc. Accordingly, the product of the present invention can prevent liver damage caused by peroxidized lipids.

Example 6

The present practical example concerns anti-mutagenic action. The process of koji preparation according to the present invention was performed on two types of raw materials, i.e., whole soybeans and defatted soybeans; and respective products prepared by hot air draft drying following koji preparation and hot air draft drying following hydrolysis were subjected to a test in which the suppression rate of the SOS induction reaction of Salmonella typhimurium was measured by MNNG in order to ascertain the respective anti-mutagenic properties.

TABLE 15

|  | Suppression rate (%) |
| --- | --- |
| Whole soybeans | Untreated 22.5 |
|  | Following koji preparation 15.2 |
|  | (product dried by hot air draft) |
|  | Following hydrolysis 60.2 |
|  | (product dried by hot air draft) |
| Defatted | Untreated 0.8 |
| soybeans | Following koji preparation 24.5 |
|  | (product dried by hot air draft) |
|  | Following hydrolysis 34.7 |
|  | (product dried by hot air draft) |

The measurement results were as shown in Table 15 above. The suppression rate following hydrolysis tended to be highest; and it appears from this that Maillard reaction products were produced by hydrolysis. Thus, in the present invention, a Maillard reaction occurs in the same manner as in miso; and there is no addition of salt as there is in miso or soy sauce. Accordingly, the hydrolysis time following koji preparation can be greatly shortened.

The present invention is by no means restricted to the above-described embodiments and examples, and various modifications may be made as necessary.

What is claimed is:

1. A process for preparing a product containing a health-promoting component, characterized in that: a health-promoting component is produced by inoculating koji mold on a pulse crop to effect koji preparation, and then hydrolyzing, through an addition of water, products produced by said koji preparation treatment, and a product containing said health-promoting component is produced by adding intestine-regulating bacteria in single-stomached animals which constitute a health-promoting component to said pulse crop and growing said bacteria during a period extending from said inoculation of said koji mold to a completion of said hydrolysis.

2. A process for preparing a product containing a health-promoting component according to claim 1, characterized in that said bacteria which have an intestine-regulating effect in single-stomached animals are added simultaneously with said inoculation of said koji mold.

3. A process for preparing a product containing a health-promoting component according to claim 1 or 2, characterized in that said bacteria which have an intestine-regulating effect in single-stomached animals consist of lactic acid bacteria which have an intestine-regulating effect in single-stomached animals.

4. A process for preparing a product containing a health-promoting component according to claim 1 or 2, wherein said health-promoting component produced by said koji preparation treatment and hydrolysis treatment comprises at least one member selected from the group consisting of liver function improving constituents, cardiac function improving constituents, anti-inflammatory constituents, antifat constituents, antioxidation consititents and antimutagen constituents.

5. A process for preparing a product containing a health-promoting component according to claim 1, or 2, wherein said health-promoting component produced by said koji preparation treatment and hydrolysis treatment are formed so as to be absorbed by a digestive tract.

6. A process for preparing a product containing a health-promoting component according to claim 3, wherein said health-promoting component produced by said koji preparation treatment and hydrolysis treatment comprises at least one member selected from the group consisting of liver function improving constituents, cardiac function improving constituents, anti-inflammatory constituents, antifat constituents, antioxidation consititents and antimutagen constituents.

7. A process for preparing a product containing a health-promoting component according to claim 3, wherein said health-promoting component produced by said koji preparation treatment and hydrolysis treatment are formed so as to be absorbed by a digestive tract.

8. A process for preparing a product containing a health-promoting component according to claim 4, characterized in that said health-promoting component produced by said koji preparation treatment and hydrolysis treatment are formed so as to be absorbed by a digestive tract.

9. A process for preparing a product containing a health-promoting component according to claim 6, wherein said health-promoting component produced by said koji preparation treatment and hydrolysis treatment are formed so as to be absorbed by a digestive tract.

* * * * *